United States Patent [19]
Pappas et al.

[11] Patent Number: 5,824,096
[45] Date of Patent: Oct. 20, 1998

[54] HINGED KNEE PROSTHESIS WITH CONDYLAR BEARING

[75] Inventors: Michael J. Pappas, Stuart; Frederick F. Buechel, Naples, both of Fla.

[73] Assignee: Biomedical Engineering Trust I, N.J.

[21] Appl. No.: 354,480

[22] Filed: Dec. 12, 1994

[51] Int. Cl.⁶ .................................................. A61F 2/38
[52] U.S. Cl. ............................................................ 623/20
[58] Field of Search ............................ 623/16, 18, 19, 623/20, 21

[56] References Cited

U.S. PATENT DOCUMENTS

| | | |
|---|---|---|
| 4,092,740 | 6/1978 | Eshiriqui . |
| 4,206,517 | 6/1980 | Pappas et al. . |
| 4,219,893 | 9/1980 | Noiles . |
| 4,470,158 | 9/1984 | Pappas et al. . |
| 4,888,021 | 12/1989 | Forte et al. . |
| 5,139,521 | 8/1992 | Schelhas ................................. 623/20 |
| 5,314,481 | 5/1994 | Bianco .................................... 623/20 |
| 5,370,701 | 12/1994 | Finn ........................................ 623/20 |

FOREIGN PATENT DOCUMENTS

| | | |
|---|---|---|
| 0472475 | 2/1992 | European Pat. Off. ................ 623/20 |
| 2641966 | 7/1990 | France ................................... 623/20 |
| 22 44 064 B1 | 3/1974 | Germany . |
| 25 45 821 | 4/1976 | Germany . |
| 35 29 894 A1 | 3/1987 | Germany . |
| 3529894 | 3/1987 | Germany ............................... 623/20 |
| 4021198 | 9/1994 | WIPO .................................... 623/20 |

OTHER PUBLICATIONS

Buechel, Frederick F., *nj LCS Tricompartmental Knee System with Porocoat.*

Primary Examiner—David Isabella
Attorney, Agent, or Firm—Anthony J. Casella; Gerald E. Hespos; Ludomir A. Budzyn

[57] ABSTRACT

A femoral component with a femoral stabilizing implanted rod has condylar surfaces of different radii which mate with a mating tibial platform is stabilized in the tibia with a rod, the bearing translating on the platform in the posterior-anterior directions in response to knee flexion and extension. The bearing bears the full extension load on congruent articulating contact regions with the condylar surfaces and lesser flexion loads via incongruent articulating contact. A hinge assembly is pinned to the femoral condylar component through a head having a depending shaft fixed to a thermoplastic tapered bearing axially floating and rotatably movable in a tibia platform component mating cavity. The head passes through the bearing and stops the bearing translations at extreme posterior and anterior positions. In a second embodiment, a projection on the tibial component mates in a recess in the bearing for controlling and limiting the amount of axial rotation of the femoral component relative to the tibial component as a function of the extent of flexion in a knee joint.

32 Claims, 11 Drawing Sheets

HINGED KNEE PROSTHESIS WITH CONDYLAR BEARING

This invention relates to hinged protheses and, more particularly, to knee prostheses with a hinge and a condylar bearing.

Hinge type knee prostheses such as described by Noiles U.S. Pat. No. 4,219,893 are generally used where the natural collateral ligaments are absent or incompetent to provide knee stability with a resurfacing type knee replacement such as that described by Pappas and Buechel in U.S. Pat. No. 4,470,158, incorporated by reference herein. In the latter replacement, hinge elements are not used.

Hinge type prostheses typically transmit most of the joint loading from the femur to the tibia through the hinge. Such load transfer requires relatively large hinge elements including a hinge pin, hinge bearings and hinge housing. Such designs require considerably greater removal of bone for implantation than the non-hinge type resurfacing replacement protheses described in the Pappas et al. patent. The greater bone removal is required in order to accommodate the hinge elements. Further, hinge type knee replacements are typically significantly heavier than resurfacing type knee replacements.

Further, as disclosed in the Pappas et al. U.S. Pat. No. 4,470,158, for example, the femoral element for a knee has a complex curved surface defined by different radii. As the tibia rotates relative to the femur, it rotates about different axes as defined by the femur element bearing surface. Such different axes complicates the use of a hinge type device with such bearing surfaces since hinges typically rotate about an axis fixed in a plane which is rotatable about a second axis as exemplified by Noiles discussed above; Forte, U.S. Pat. No. 4,888,021; Eshriqui, U.S. Pat. No. 4,092,740; German Offenlegungsschrift 25 45 821 and German Auslegeschrift 22 44 064. The latter illustrates a hinge pin which slides in a slot in the mating element. However, the mating femur and tibia elements are in contact directly with each other. Regardless, such elements tend to be undesirably large as previously discussed to accommodate the large loadings.

The present inventor, according to the present invention, recognizes a need for a condylar bearing hinge knee prosthesis utilizing the bearing arrangement disclosed by Pappas et al. discussed above. It is recognized that in this combination the bearing arrangement is used to transfer most of the loading from the femur to the tibial through the condylar surfaces of the femoral and tibial components. The hinge, in contrast to the prior art devices, in accordance with the present invention, is used only for knee stabilization rather than load transfer. This allows the use of relatively small hinge elements producing a lighter weight device which requires significantly less removal of bone than typical hinge load bearing knee replacements.

Minimizing bone removal is desirable since implant fixation is often improved where more bone is retained and also in the event of the development of a need to replace the prosthesis due to prosthetic loosening or failure. Minimizing the weight of the prosthesis is desirable in order to minimize the effect of prosthesis weight on gait.

A prosthetic joint for accommodating articulation between a first bone and a second bone according to the present invention comprises a first element for attachment to a first bone, the first element having a first surface facing substantially away from the first bone and a second element for attachment to a second bone generally along a first axis, the second element having a second surface facing substantially away from the second bone. Bearing means are between and in articulating contact with the first and second surfaces for transferring substantially all of the load from the first element to the second element.

Hinge means include a member for attachment to the second element and hinged to the first element, the member being secured to the second element such that the hinge means transfers relatively negligible load from the first bone to the second bone in a direction along the first axis and for supporting the first and second bones in a direction transverse the first axis.

In accordance with a further embodiment, a prosthetic joint for accommodating articulation between a first bone and a second bone comprises a first element for attachment to a first bone, the first element having a first surface facing substantially away from the first bone and a second element for attachment to a second bone generally along a first axis, the second element having a second surface lying in and defining a plane transverse the first axis and facing substantially away from the second bone.

Bearing means are between and in articulating contact with the first and second surfaces, the bearing means having a third surface in contact with the first surface and a fourth surface in contact with the second surface, the bearing means and surfaces being constructed for displacement in a direction transverse to the first axis in response to articulation of the first element relative to the second element.

Hinge means are included for hinged attachment to the first element for rotation about a second axis transverse the first axis, the hinge means for attachment to the second element for rotation about the first axis.

In a further embodiment, the latter hinge means are secured for rotation about and axial displacement along the first axis in non-load bearing relation to said bones in a direction along the first axis while stabilizing the bones transversely the first axis.

In a still further embodiment, a prosthetic joint for accommodating articulation between a first bone and a second bone includes a first element for attachment to the first bone and has a first surface facing substantially away from the first bone; a second element for attachment to the second bone generally along a first axis and having a second surface facing substantially away from the second bone; the bones exhibiting flexion and extension; and means coupled to the first and second elements for permitting the second element to rotate relative to the first element about the first axis.

The improvement therewith comprises rotation limiting means for limiting the value of the angular extent of relative rotation between the first element and the second element about the first axis as a function of the extent of flexion.

Figure 1:
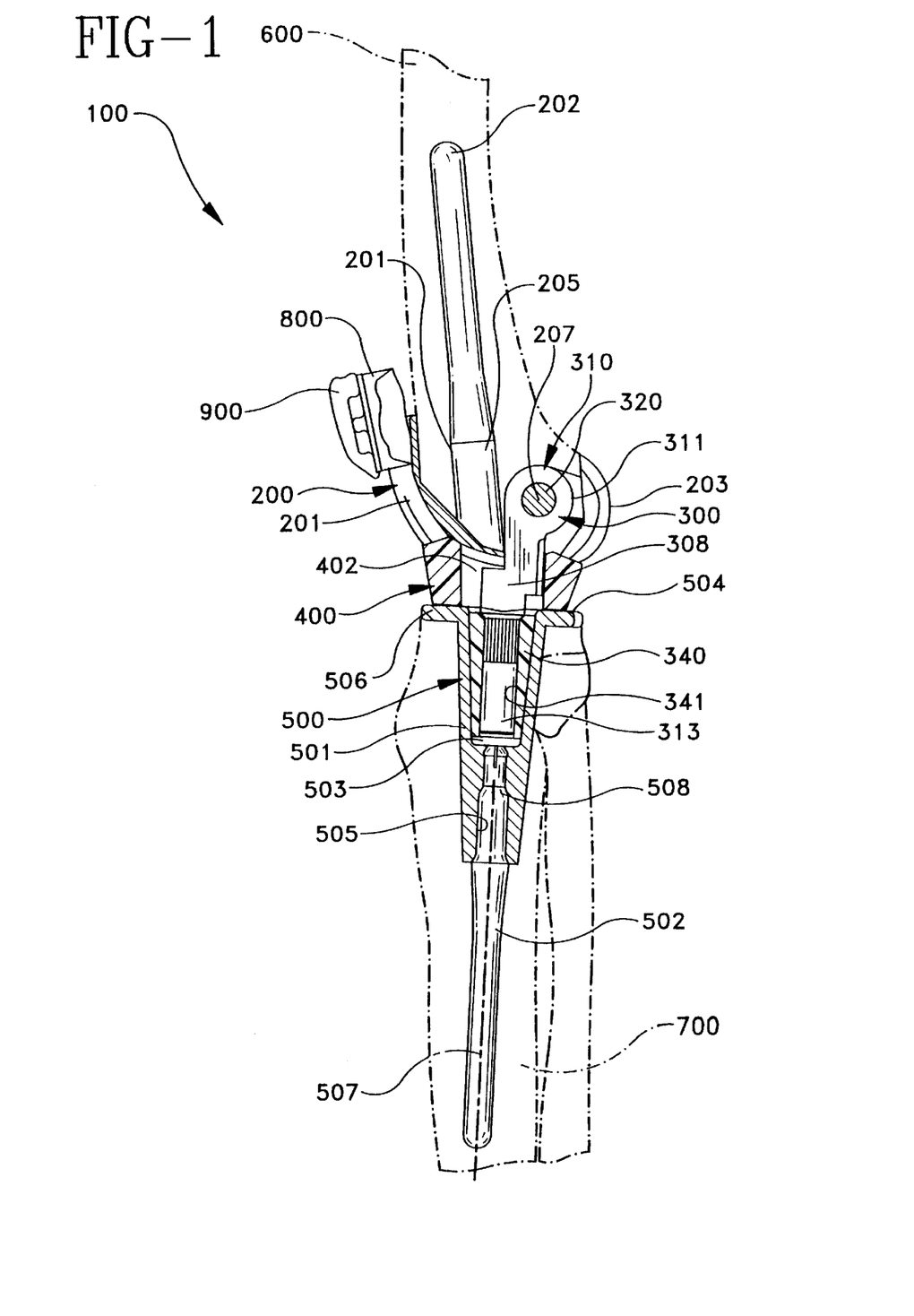
FIG. 1 is a side elevation sectional view of a hinged knee replacement prothesis according to an embodiment of the present invention.

In FIG. 1, hinge knee replacement device 100 comprises a femoral component 200, hinge assembly 300, bearing 400, and tibial component 500. The device 100 is implanted into the femur 600 and tibia 700. A patellar component 800 may also be implanted into the natural patella 900, or the natural patella may be retained.

The femoral component 200 comprises a metal femoral body 201 including a rod support 205 and a stabilizing rod 202 which is assembled to support 205 and implanted in the femur 600. The femoral body 201, FIG. 2, has a pair of like spaced apart condylar members 208 joined by a connecting member 209. Polished articular curved male condylar surfaces 203 are formed on each member 208. Each of the surfaces 203, FIG. 3, comprises curved segments $S_2$, $S_3$ and $S_4$, FIG. 3, with lateral different radii $R_2$, $R_3$, and $R_4$, respectively. The segments form a smooth surface in which the radii at the interface between adjacent surface segments have common tangents. The surfaces 203 are joined by a common connecting curved surface 214 in the region of member 209, FIG. 2. A detailed description of the formation of the femoral condylar articulating surfaces 203 is given in the aforementioned Pappas et al. patent incorporated herein by reference and need not be provided further herein.

Figure 2:
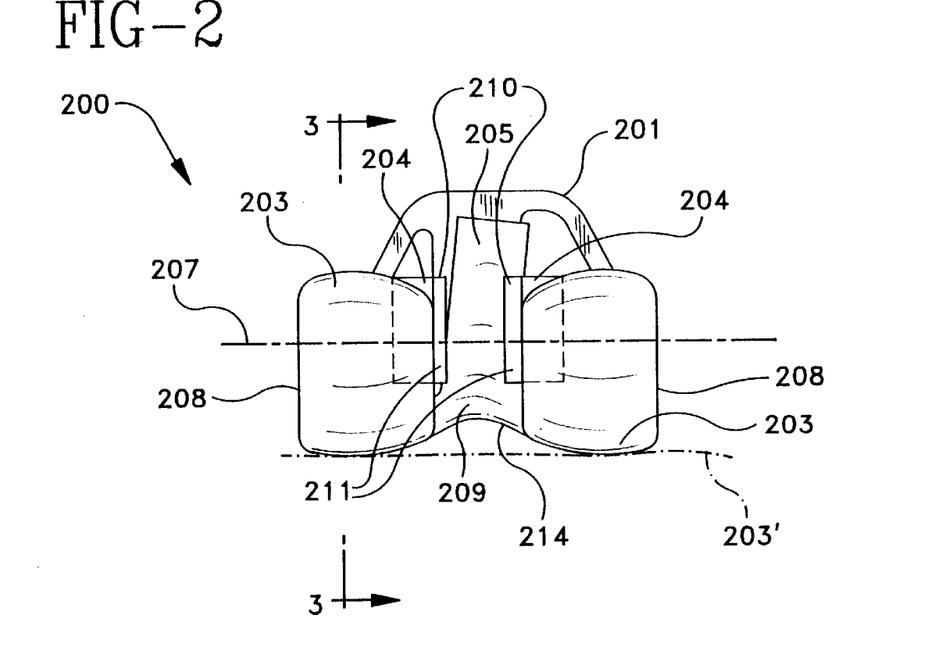
FIG. 2 is a posterior side elevation view of the femoral component of the embodiment of FIG. 1.
Figure 3:
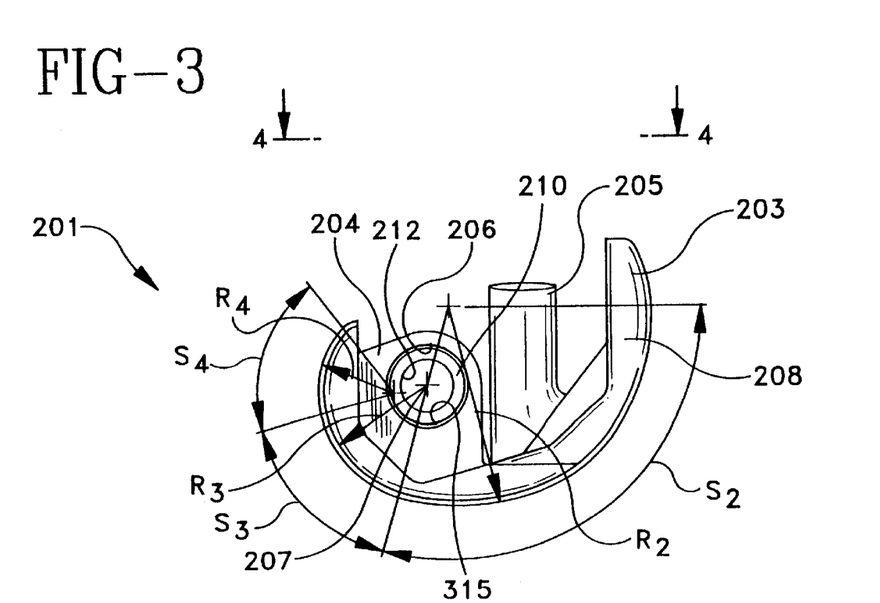
FIG. 3 is a side elevation view of the component of FIG. 2 taken along lines 3—3.
Figure 4:
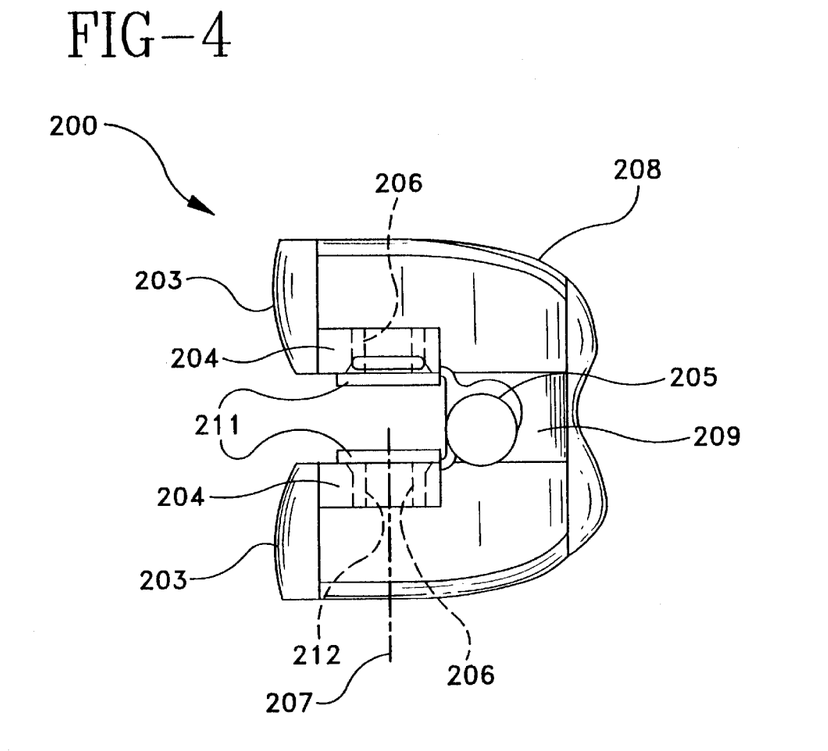
FIG. 4 is a plan view of the component of FIG. 3 taken along lines 4—4.

In FIGS. 2–4, two spaced apart hinge supports 204 and a hollow core rod support 205 are formed in and project from the body 201. The hinge supports 204 are each integral with and part of the corresponding condylar member 208. Each support 204 has a bore 206 which is aligned on and concentric with axis 207 may be parallel to a line 203' which is tangent to surfaces 203. Two like thermoplastic cylindrical bushings 210 each including thrust flanges 211 and having a bore 212 forming a hinge bearing surface are pressed fitted into bores 206 in the hinge supports 204.

Figure 12:
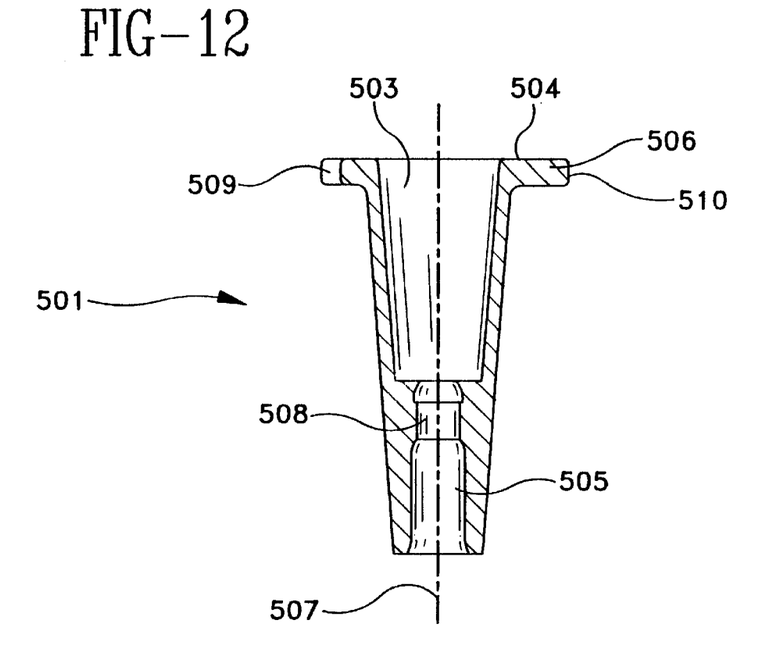
FIG. 12 is a side elevation sectional view of the tibial component of the embodiment of FIG. 13 taken along lines 12—12.

The tibial component 500, FIG. 1, comprises a metal tibial body 501 and a stabilizing rod 502 having an end 508 assembled to body 501 in support cavity 505. The rod 502 is implanted in the tibia in a known manner. In FIG. 12, elongated cylindrical cavity 505 is formed in tibial body 501. Cavity 505 is concentric with axis 507 for receiving an end of the stabilizing rod 502. The tibial body 501 has a plate 506 at one end transverse axis 507.

Figure 13:
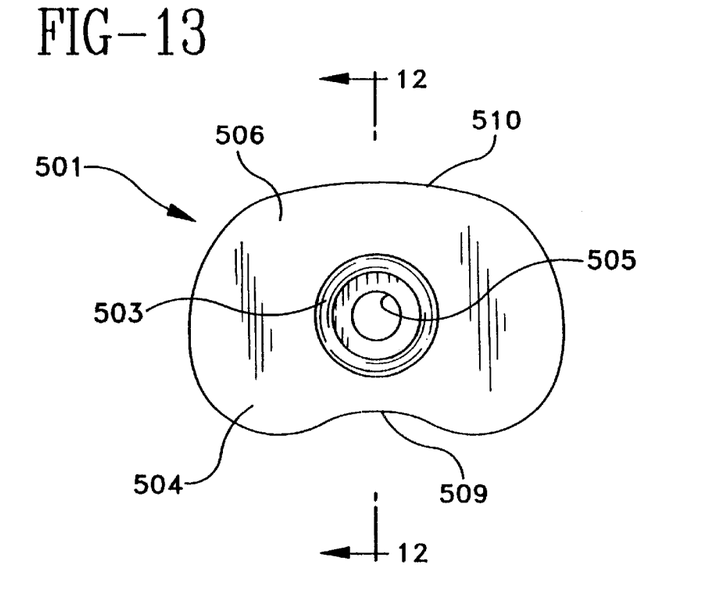
FIG. 13 is a plan view of the tibial component of FIG. 1.

Plate 506 has a polished planar surface 504 normal to axis 507. Plate 506 is provided in different thicknesses to accommodate corresponding amounts of tibial bone loss. A frustro-conical cavity 503 is formed in body 501 concentric about axis 507. Cavity 503 is in communication with cavity 505 via a reduced diameter portion 508. Plate 506, FIG. 13, is elongated with a convex curved peripheral edge 510. The plate 506 has a radially inwardly extending curved concave recess 509 opposite edge 510. Cavities 503 and 505 are aligned on axis 507 centrally of the plate 506.

The hinge assembly 300, FIGS. 1, 5–7, 14 and 15 includes a metal carriage 310 with a head 311, hinge pin 320 and a set screw 330. Head 311 has a hinge pin support bore 315. A screw hole 316 in head 311 is in communication with bore 315 for receiving screw 330, Fig.15. An intermediate rectangular in transverse section shank 308 depends from head 311, FIGS. 6 and 7. Shank 308 has polished planar sides 312, a planar polished posterior face 317 and a planar polished anterior face 318. A circular cylindrical shaft 313 depends from shank 308. Shaft 313 has an annular extending raised knurl 314 on its peripheral surface adjacent to shank 308.

Figure 5:
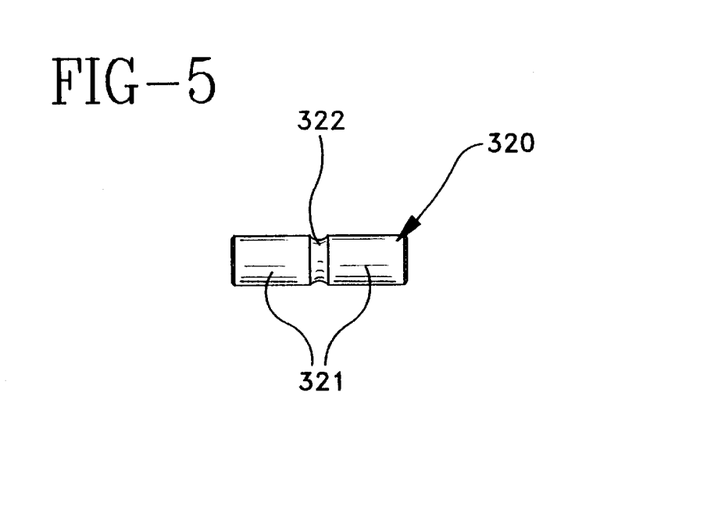
FIG. 5 is a side elevation view of the hinge pin used in the embodiment of FIG. 1.

Metal circular cylindrical hinge pin 320, FIG. 5, has polished pin bearing surfaces 321 spaced by annular groove 322. A set screw 330, FIG. 15, is used to hold the hinge pin 320 in the hinge pin support bore 315 by engaging groove 322 in the hinge pin 320. The hinge pin 320 is rotatably and closely received in bores 212 of plastic bushing 206, FIGS. 4 and 14, mounted in supports 204 of body 201.

Figure 7:
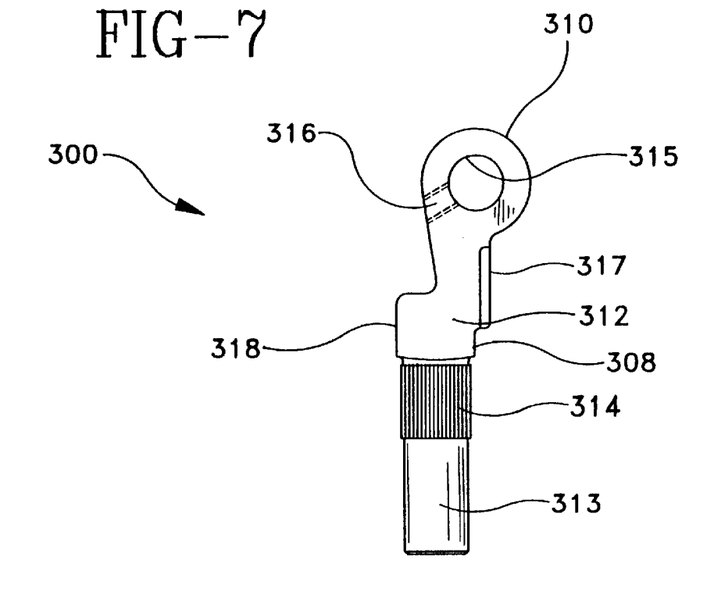
Figure 8:
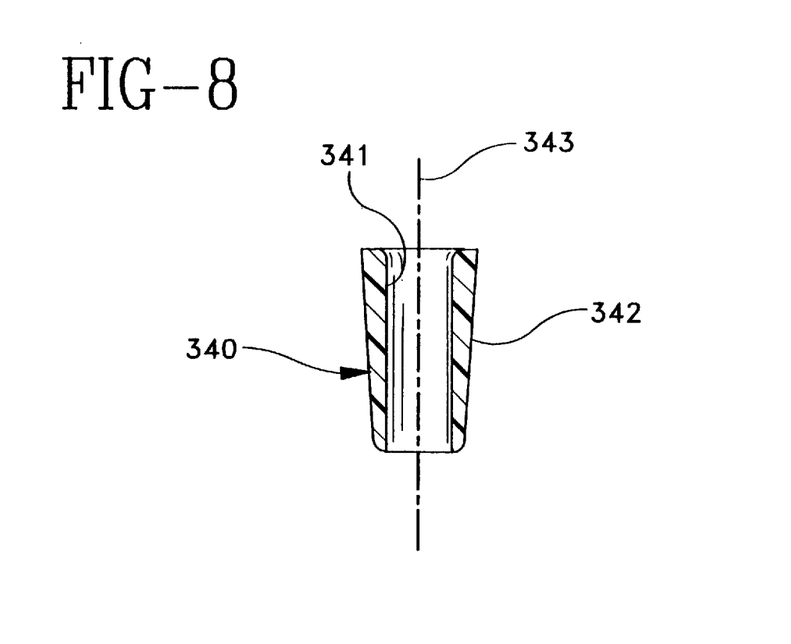
FIG. 8 is a side elevation sectional view of a thermoplastic bearing insert for receiving the rod portion of the hinge member of FIGS. 6 and 7.

A thermoplastic bushing 340, FIG. 8, has a frustro-conical outer bearing surface 342 concentric with axis 343. Bushing 340 has an axial extending circular cylindrical bore 341 concentric with axis 343. Shaft 313, FIGS. 6, 7, 14 and 15, is press fit into the bushing 340 bore 341 with the knurls 314 engaged with the bore 341 surface to form a relatively fixed unitary integral assembly with the bushing 340.

The bushing 340 outer bearing surface 342 with the shaft 313 attached is axially inserted along axis 507 into the frustro-conical cavity 503 of body 501 with the axes 343 and 507 substantially coaxial. The bushing 340 is so dimensioned such that it can displace axially in the cavity 503 of body 501 as shown, for example, by comparison of the position of the bushing in the body 501 cavity 503, FIGS. 14 and 15.

Figure 14:
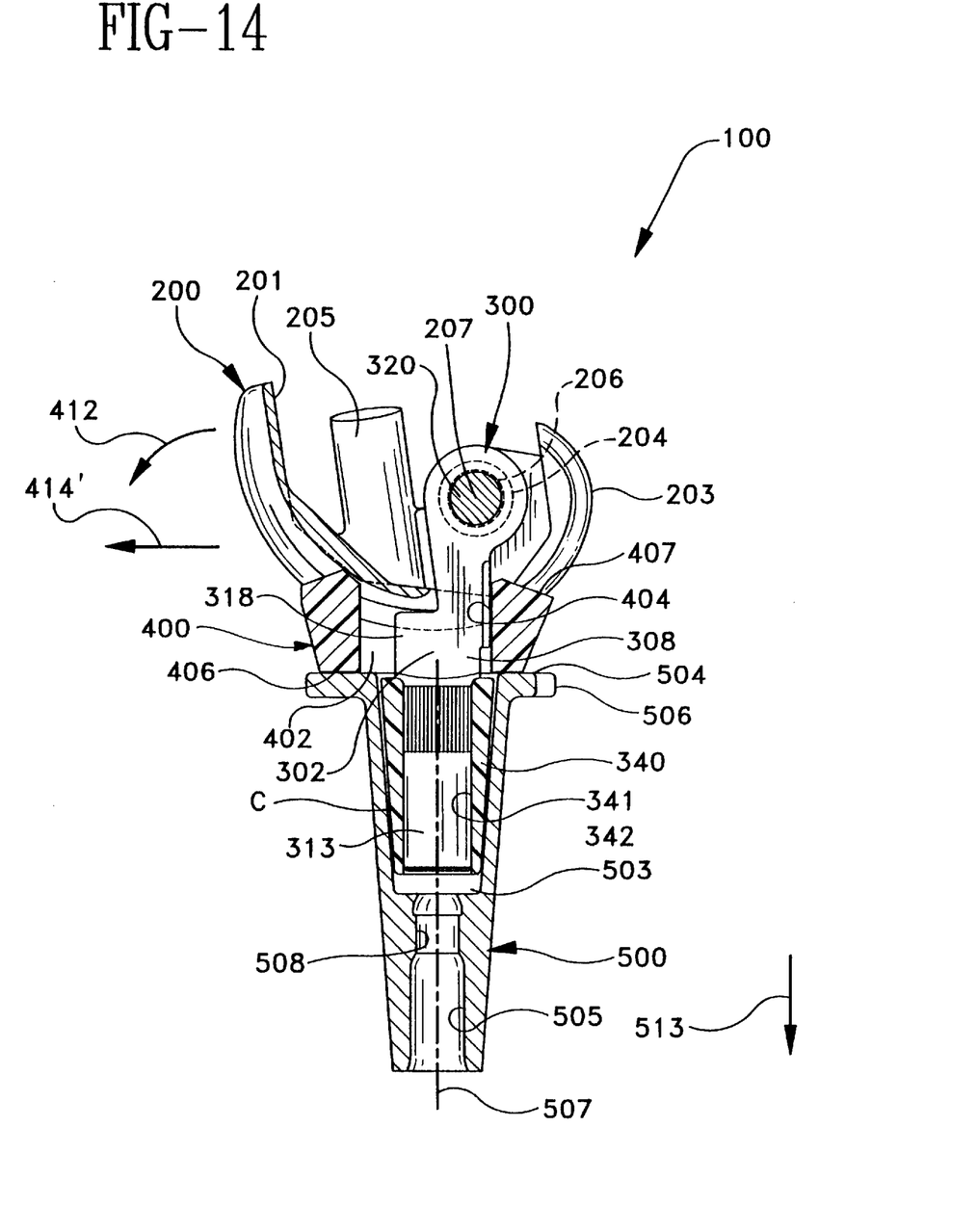
FIG. 14 is a side elevation sectional view of the prothesis of FIG. 1 in the knee extension position.
Figure 15:
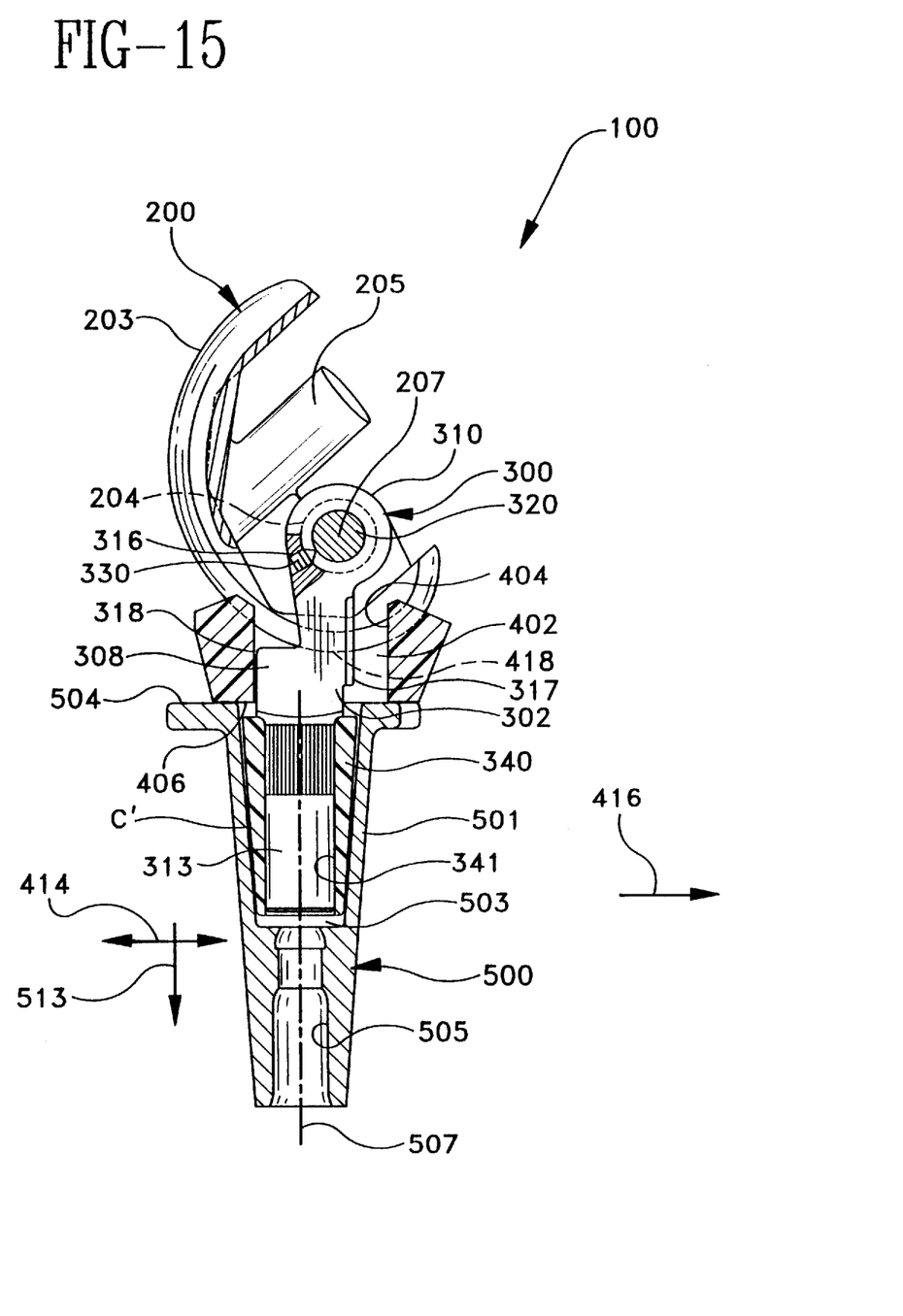
FIG. 15 is a side elevation sectional view of the prothesis of FIG. 1 in a knee flexion position.

In the axial position of FIG. 14, with the bones 600 and 700 (FIG. 1) in extension, the bushing 340 has a radial clearance C between its tapered outer bearing surface 342 and the tapered inner surface of cavity 503. Clearance C is exaggerated for purposes of illustration. Clearance C has a value sufficient to permit the bushing 340 to axially displace in direction 513 further into the cavity 503 to the position shown in FIG. 15 from the position of FIG. 14 with negligible axial loading on the body 501 by bushing 340.

The bushing 340 surface 342 articulates with the polished inner tapered bearing surface of cavity 503 of the tibial body 501, FIG. 14, about axis 507. Due to the clearance C, there may be some transverse radial play and motion between the bushing 340 and the surface of cavity 503, but this play is acceptable.

In FIG. 15, the shaft 313 and bushing 340 are in a flexion axial position and are readily shifted downwardly in the Figure in direction 513 relative to their position of FIG. 14. In this flexion position there is a clearance C' (not visible in the Fig.) between the bushing 340 and the cavity 503 surface. As a result, there is negligible axial load induced by shaft 313 on to body 501 in direction 510 in either the full extension or full flexion positions. Thus the hinge assembly 300 shaft 313 and bushing 340 in bore 503 is supported substantially only in the transverse directions, FIGS. 14 and 15, normal to axis 507. This is important to provide stability to the bones 600 and 700 (FIG. 1) in all radial directions transverse axis 507 such as directions 414.

Figure 9:
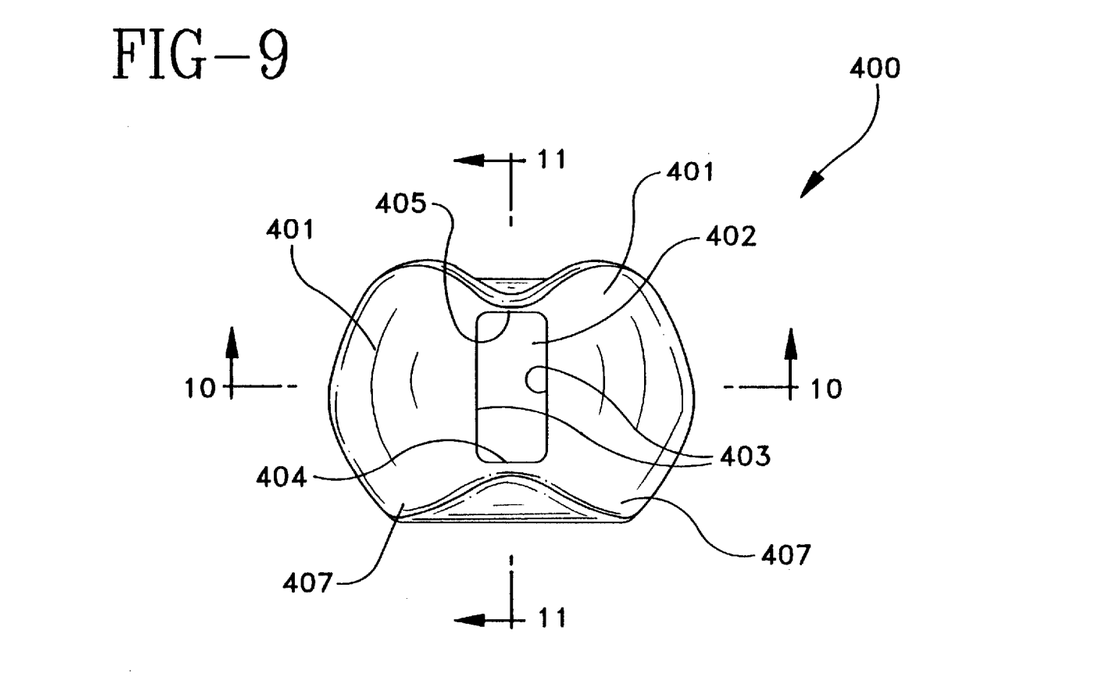
FIG. 9 is a plan view of the tibial condylar bearing surfaces of the bearing of the embodiment of FIG. 1.
Figure 10:
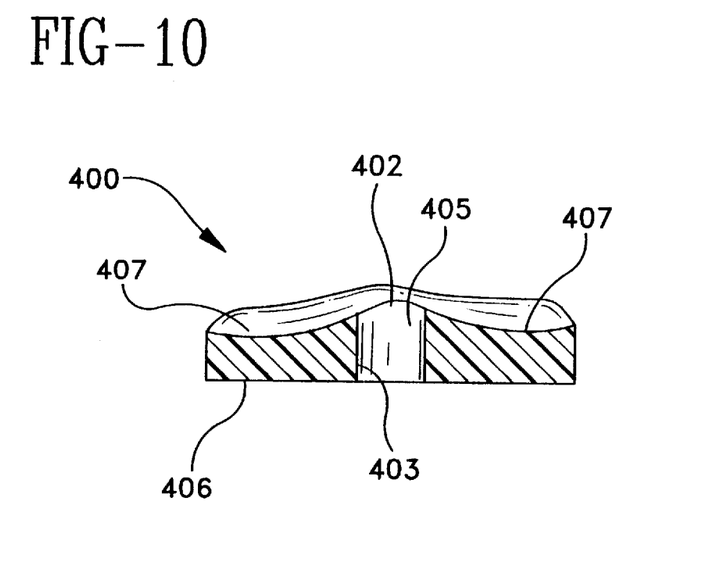
FIGS. 10 and 11 are elevation sectional views of the bearing of FIG. 9 taken along respective lines 10—10 and 11—11.
Figure 11:
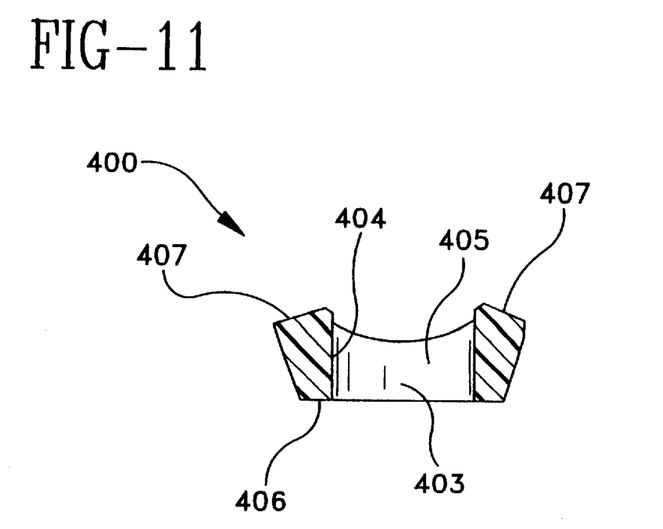

Thermoplastic bearing 400, FIGS. 9–11, includes tibial condylar bearing surfaces 401 which are shaped to receive the femoral condylar surfaces 203 of members 208. The bearing 400 construction is provided in more detail in the Pappas et al. patent referred to above in the introductory portion. The bearing surfaces 401 articulate with the mating femoral condylar articulating surfaces 203.

Figure 6:
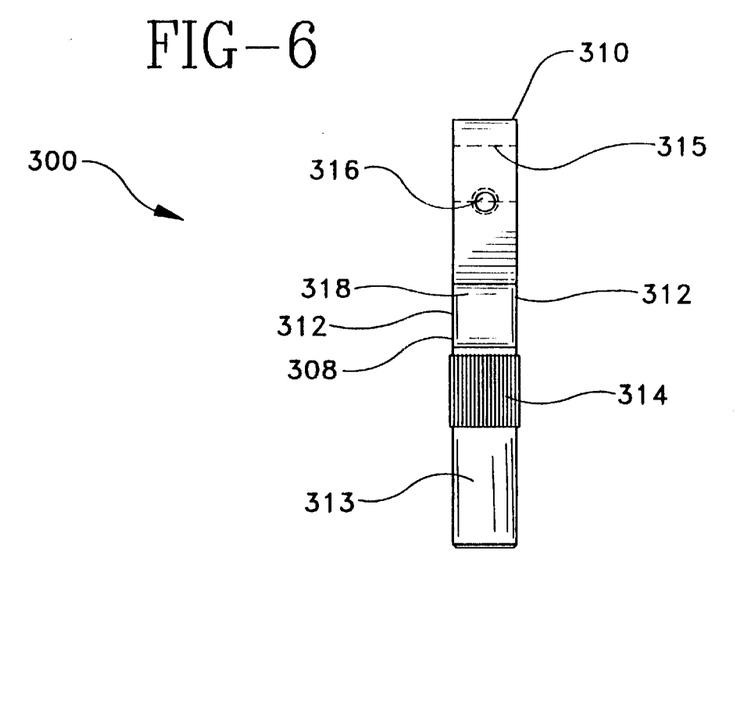
FIGS. 6 and 7 are respective anterior and side elevation views of a metal carriage member of the hinge assembly of the embodiment of FIG. 1.

The bearing 400 has a through slot 402 rectangular in plan view, FIG. 9, which slidably receives the carriage head 311 shank 308, FIGS. 6 and 7, therethrough. The slot 402 has parallel planar sides 403. Sides 403 engage the carriage shank sides 312 to prevent axial rotation of the bearing 400 relative to the carriage 310 about axis 507, FIGS. 14 and 15. Posterior bearing slot 402 end 404 and anterior slot end 405 engage the posterior and anterior faces 317 and 318, respectively, of the carriage head 311 shank 308 during the displacement from extension to flexion and vice versa motions of the knee. These engagements are shown in FIGS. 14 and 15.

Inferior planar smooth finished bearing surface 406 articulates with the polished, superior tibial surface 504 of the tibial body 501 on plate 506. The condylar bearing regions 401 of surfaces 407 are complementary to segment $S_2$ of the femoral articular surface 203 to form the tibial articulating surface 407. As shown in FIG. 14, these mating surfaces are congruent during extension when the bearing bears the greatest load. In contrast, during flexion, FIG. 15, condylar surface segments S3 or S4, FIG. 3, engage the bearing surface 407 and provide incongruent contact, i.e., line contact.

FIG. 14 shows a partial cross section of the assembled hinge knee replacement, excluding the stabilizing rods 202 and 502, in full extension. The line 410 corresponds to the engaged articulating surfaces of the femoral body 201 and bearing 400 illustrating their congruent contact in this motion phase. Further extension in direction 412 is stopped by the posterior face 317 of carriage 310 shank 308 engaging posterior slot end 404. This stopping action also prevents further anterior translation displacement of the bearing 400 relative to the tibial body 501 in anterior direction 414'.

The bearing 400 translates in anterior direction 414' in response to the camming action of the engaged articular femoral body 501 surface 203 when the joint is articulated from the flexion position of FIG. 15 to the full extension position of FIG. 14. The camming action attempts to move the bearing 400 anteriorly. The anterior bearing motion is the result of the anterior motion of the center of radius $R_2$ of femoral body 201 (FIG. 3). This anterior motion is due to the counter clockwise rotation from the position of FIG. 15 to that of FIG. 14 relative to the tibial body 501, about the center of the body 201 hinge support bores 206 during extension.

Since the bearing articulating surface 407 is held against the femoral articular surface 203 due to the joint compressive load, the center of the tibial articular surface 407 radius, and thus bearing 400 must move anterior, direction 414', with the center of $R_2$. The bearing 400 moves in this direction until stopped by shank 308. This stopping action is soft and gradual due to the camming action of the condylar surface 203 on bearing surface 407.

FIG. 15 shows the knee replacement in moderate flexion. In this phase of knee motion the tibial articular surface 407 is under compressive contact with segment $S_3$ of femoral articular surface 203. This compressive force will drive the bearing 400 in posterior direction 416 to the posterior position of FIG. 15 from the bearing anterior flexion position of FIG. 14. The engagement of condylar surface 203 with the bearing surface 407 is illustrated by phantom lines 418.

In FIG. 15, a line connecting the body 201 articular surface 203 radius $R_2$ (FIG. 3) with the origin of radius $R_3$ at axis 207 (the hinge pin center) is parallel to the compression force vector (not shown). Since the compressive force vector is approximately along the axis 507 of the tibial component 500 body 501 this motion of the body 501 from the position of FIG. 14 to that of FIG. 15 will result in a posterior translation of the bearing 400 in direction 416. Excessive posterior positioning of the bearing 400 is prevented by the engagement of the anterior face 318 of carriage 310 shank 308 with the anterior slot end 405 of the slot 402 in bearing 400.

The bushing 340, because it is loosely engaged in the tibia component body 501 cavity 503, and is of the same tapered configuration as the cavity 503, is also free to rotate about the tibial axis 507 as well as axial translate along this axis as discussed above. The shaft 313 of the hinge assembly 300 thus also has the same motions since the shaft is fixed to the bushing 340. Therefore, the hinge knee replacement 100 thus has two degrees of freedom of motion; flexion-extension about the hinge axis 207 and axial rotation about a tibial axis 507.

Preferred metal materials for the different components are titanium alloy with a ceramic titanium nitride coating or cobalt chromium alloy. The preferred thermoplastic is ultra-high molecular weight polyethylene (UHMWPe).

The knee replacement 100 is implanted in the following manner. An appropriate femoral stabilizing rod 202 is assembled to the femoral body 201, FIG. 1, in a known manner to form femoral component 200. The bearing 400 is assembled onto a carriage subassembly, consisting of the carriage 310 and tapered bushing 340, with slot 402 of the bearing 400 engaging shank 308 of the carriage. The head 311 is then inserted into the region between bushings 210 previously assembled to the femoral component 200, FIG. 4.

The head 311 support bore 315 (FIG. 7) is then aligned with the hinge bearing surfaces 212 of bushings 210, FIG. 4. The hinge pin 320 is passed through a first hinge bearing bore 212, through support hole 315 of the carriage 310 and into the second hinge bearing bore 212. The set screw 330 is then introduced into set screw hole 316, FIG. 15. As the set screw 330 is tightened its conical end engages groove 322 in the hinge pin 320, FIG. 5, clamping the pin and the set screw into place. Such clamping is important to avoid metal-to-metal micromotion between the pin 320 and head 311 and thus the generation of harmful metallic wear debris. The tibial body 501 and tibial stabilizing rod 502 are then assembled to form tibial component 500.

The tibia and femur are prepared in the manner described in a brochure entitled *nj LCS® Tricompartmental Knee System with Porocoat®* by Frederick F. Buechel, 1993, except reamers are used to prepare channels to receive the femoral and tibial stabilizing rods 202 and 502, respectively. A box-like cavity is prepared in the central, distal, posterior aspect of the femur. This box-like cavity comprises an envelope for surrounding the two supports 204, FIG. 4. The tibial component 500 is implanted into tibia 700 and the femoral component—hinge assembly is implanted into femur 600.

Figure 19:
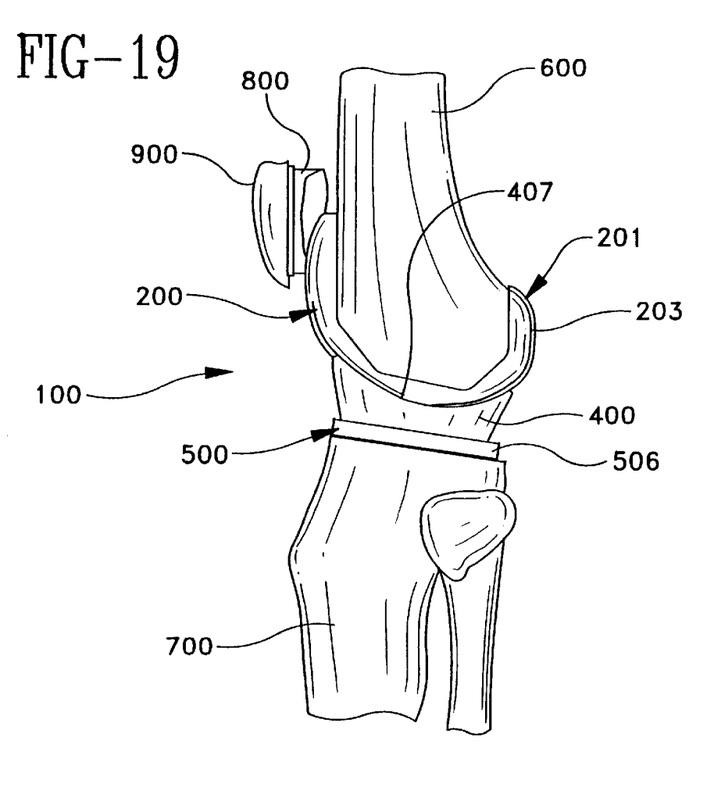
FIG. 19 is a side elevation view of the prothesis of FIG. 1 as implanted.

The joint is then distracted and the tapered bushing 340 is inserted into the tapered cavity 503 of the tibial body 501. A tapered bushing is used in preference to a cylindrical bushing to allow some misalignment between the tapered bushing, 340 and cavity 503 during this insertion. The joint is then closed completing the implantation. The implanted prosthesis as it appears externally is shown in FIG. 19.

Figure 16:
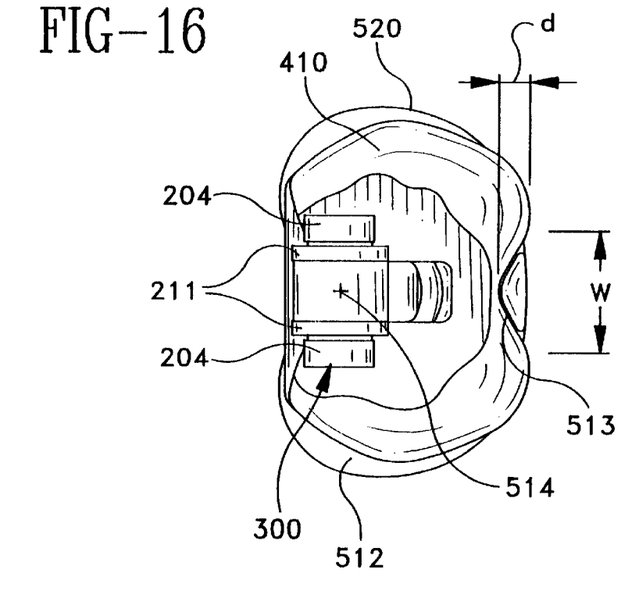
FIGS. 16–18 are plan views of an alternate embodiment of femoral and tibial components illustrating axial rotation position limiting structure.
Figure 17:
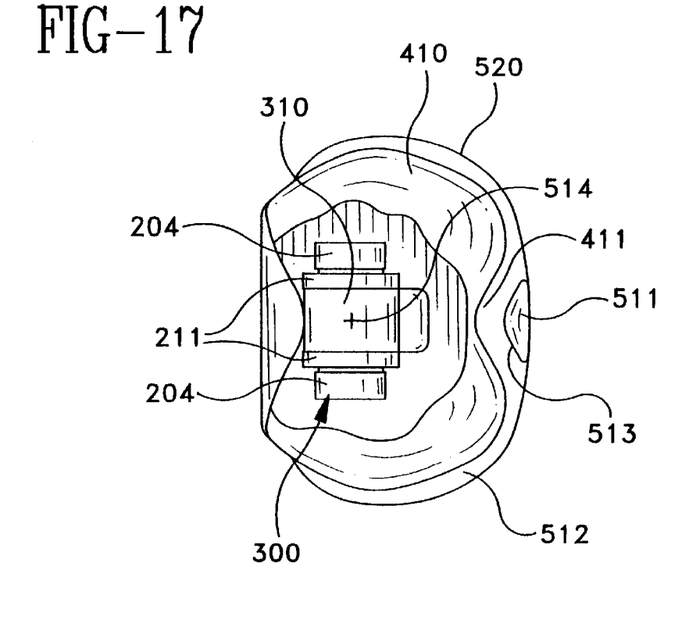
Figure 18:
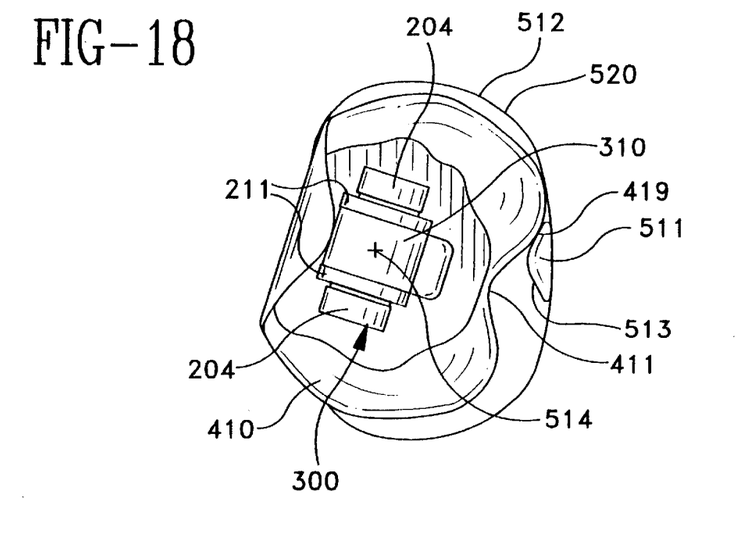

In FIGS. 16–18, an alternate embodiment of a tibial body 520 includes an anterior projection 511 upstanding from and fixed to (e.g., integral with) the body 520 platform 512. The femoral condylars are broken away in these figures for simplicity of illustration. Projection 511 has a somewhat V-shaped, but smooth curved surface 513 which engages an anterior recess 411 of similar shape but larger dimensions in bearing 410. FIG. 18 shows the bearing 410 in the anterior position at full extension. The recess 411 has a greater width w, FIG. 16, than that of projection 511 in a direction transverse the anterior-posterior translation of the bearing 410. The recess 411 has a depth d greater than the thickness of the projection in the depth direction.

The engagement of projection 511 with recess 411 in the fully seated and full extension position of FIG. 16 prevents axial rotation of the femoral component relative to the tibial component such as about axis 514. When implanted, this engagement prevents the axial rotation of the femur relative to the tibia during full extension.

This lack of axial rotation at full extension is normal in the human knee and may be desirable in some patients that cannot exercise muscular control of axial rotation. As the knee is flexed, FIG. 17, the bearing 410 moves posteriorly in direction 418 causing the projection 511 to gradually disengage from the recess 411. This posterior motion gradually allows increasing angular extent of axial rotation of bearing 410 relative to body 520 about axis 514 as the posterior displacement of bearing 410 in direction 418 increases. That is, as flexion occurs, at each position of the relative flexed bones the spacing of the projection 511 from the side wall of the recess 411 increases. This increased spacing permits greater values of rotation of the projection before it abuts the recess side wall.

The shape of projection 511 and recess 411 can be configured to control axial rotation within predetermined angular limits dependent on the degree of knee flexion. Such control may also be desirable in some patients that cannot exercise muscular control of axial rotation. For example, in FIG. 16 the projection 511 prevents relative axial rotation between the femur and the tibia in full extension. In FIG. 18, in flexion, the maximum amount of axial relative rotation about axis 514 occurs as the projection 511 abuts the side wall of recess 411 at the outer rim 419 of recess 411.

In alternative embodiments, the projection 511 and bearing 410 recess 411 may have different shapes than that shown to provide further control of the angular extent of relative axial rotation as a function of flexion. For example, the taper of the recess 411 may be more gradual than that shown or steeper providing wider or narrower recesses as compared to the recess 411. The wider recess permits greater axial rotation and the narrower recess further restricts such axial rotation. In a reverse situation, the projection may be made narrower or wider accordingly.

The control of rotation in all of the embodiments is a continuous smooth function of the extent of flexion as compared to a step function. That is, as shown in FIGS. 16–18, as the body 520 moves from extension in FIG. 16 to flexion in FIG. 18, the degree of permitted rotation of the projection 511 increases as a function of the continuous smooth curved slopes of the sides of the recess 411 and the shape of the mating surfaces of the projection 511.

Also, the recess may be a slot, e.g., rectangular, and the projection may have a mating shape, e.g., rectangular, and fitted within the slot so as to preclude any axial rotation during flexion or provide a minimal rotation, as needed. By spacing the projection 511 closer to the bearing recess wall or further apart as desired, smaller or larger axial angular rotation extents may be provided. Therefore, by varying the above parameters of the recess and projection a relatively large latitude of control over the extent of axial rotation as a function of flexion can be provided.

Further, in the present embodiment, the recess 411 is formed in the bearing 410 and the projection 511 is attached to the tibial component body 520. In the alternative, should materials be available where a bearing is not needed, then the recess may be formed in one of the tibial or femoral components and the projection attached to the other component. In this case, the projection and recess are related so as permit rotation as a function of flexion. For example, the femoral component can have a recess therein or a projection that displaces anteriorly-posteriorly as the femur is rotated relative to the tibia. The important aspect is that the amount of flexion determines and is a function of the amount of axial rotation about axis 514. The function may be linear or non-linear.

The rotation value while shown to be zero at full extension in a preferred embodiment, may in other embodiments according to given implementation, be non-zero. Also, the shapes of the recess and projections do not necessarily have to be the same. What is important is that the rotation be controlled as a function of flexion. While a bearing that moves in translation is shown, such motion is not essential. Also, the degree of rotation permitted as a function of flexion can be provided with and without a hinge assembly, such as shown in FIG. 1 or other types of hinge assemblies.

Earlier condylar bearing non-resurfacing knees such as an arrangement known as the "Spherocentric" of the 1970's failed to exploit the advantages of the ability to use smaller hinge elements. Further such designs use entirely incongruent condylar contact surfaces. The hinge assembly 300 of the present invention uses relatively small hinge elements such as head 311 and pin 320 because negligible axial load is transferred to the hinge assembly 300 as discussed above.

The prosthetic joint of the present invention incorporates the bearing-condylar relationship teachings of the aforementioned Pappas et al. patent to provide a knee replacement that is congruent in the critical peak loading phase of the normal walking cycle, i.e., during extension. At the same time the joint uses reduced posterior femoral radii to produce more normal knee motion, i.e., during flexion. The reduced posterior femoral radii produce adequate line contact in the deeper flexion phases of non-critical activities and are not in contact with the tibial bearing during the congruent, critical, peak loading phase of the normal walking cycle.

Thus, the joint of the present invention provides a less bulky, lighter weight hinge type knee replacement, requiring minimal bone removal while providing the load bearing articulation and joint motion similar to that of the replacement knee described in the aforementioned Pappas et al. patent.

The articulation and motion of the aforementioned Pappas et al. patent have been proven to provide excellent clinical results after widespread clinical use for more than 15 years. The hinge knee replacement according to the present invention requires no more bone removal than a typical non-hinge type posterior stabilized knee such as the Insall-Burstein device, while providing superior stabilization with congruent contact of the stabilizing elements. Typical prior art posterior stabilized knee replacements have incongruent stabilizing elements with little, if any, stability in deep flexion.

Stability in deep flexion and extension of the joint constructed according to the present invention is provided by the hinge assembly configuration wherein the implanted rods and coupled hinge assembly components exhibit negligible motion in the transverse anterior-posterior directions 414, FIG. 15, while exhibiting negligible axial loading on the hinge assembly components in direction 513. Importantly, the bearing, such as bearing 400, displaces in the anterior-posterior directions 414 in response to the corresponding extension-flexion motions while at the same time such bearing displacements are limited by the hinge assembly.

The joint of the present invention is superior to conventional hinges since its relatively smaller hinge components allows less bone resection. This makes this hinge a candidate for cases where a prior art posterior stabilized design would be used. The joint of the present invention is superior to a prior art posterior stabilized design since it provides superior stabilization, particularly in deep flexion where stabilization is important, and does so with congruent contact of the stabilizing components, which reduces wear associated with such stabilization. Present posterior stabilized designs are entirely incongruent.

The present joint is also superior because it employs clinically proven articulating surfaces of the resurfacing LCS design of the Pappas et al. patent as discussed above. Further, the joint is superior because it employs effective axial rotation control such as available in the embodiment of FIGS. 16–18.

Further, the joint of the present invention resembles the LCS resurfacing, modular knee and uses the same instrumentation except for a simple box osteotome used to prepare a cavity for the hinge walls. Thus, it fits well within the present replacement knee systems approach. This joint further minimizes the amount of learning required by a surgeon to implant the hinge assembly familiar with the LCS approach and provides him with a familiar prosthesis for those patients needing the stability that a hinge, or posterior stabilized, knee provides.

It will occur to those of ordinary skill in this art that various modifications may be made to the embodiments described herein. The descriptions given herein are given by way of illustration and not limitation. The scope of the present invention is as defined in the appended claims.

What is claimed is:

1. A prosthetic joint for accommodating articulation between a first bone and a second bone, the joint comprising:
    a first element for attachment to a first bone, the first element having a first surface facing substantially away from the first bone;
    a second element for attachment to a second bone generally along a first axis, the second element having a second surface facing substantially away from the second bone;
    a bearing between and in articulating contact with the first and second surfaces for transferring substantially all of the load from the first element to the second element, the bearing means being configured such that the articulating contact between the bearing and the first surface enables articulation of the first element between a first angular position relative to said bearing and a second angular position relative to said bearing, the first surface being in congruent contact with the bearing in the first angular position and in incongruent contact with the bearing in the second angular position; and
    a hinge including a member for attachment to the second element and hinged to the first element, the member being secured to the second element such that the hinge transfers relatively negligible load from the first element to the second element in a direction along the first axis and for supporting the first and second elements in a direction transverse the first axis.

2. The joint of claim 1 wherein the member is rotatably secured to the first element for rotation relative to the first element about a second axis normal to the first axis.

3. The joint of claim 2 wherein the second surface is planar, the second axis being parallel to the second surface.

4. The joint of claim 1 wherein the bearing is secured for translation transverse to said first axis, said bearing for translating in response to said articulation.

5. The joint of claim 1 wherein said member is secured so as to be free to axially displace in opposite directions along the first axis relative to the second element.

6. The joint of claim 5 wherein the bearing means is secured to translate relative to the hinge means transversely said first axis.

7. The joint of claim 6 wherein the bearing translates to first and second opposite positions in response to the articulation of the first element relative to the second element, the hinge including a stop for engaging the bearing for stopping the movement of the bearing at the opposite positions during the articulation.

8. A prosthetic joint for accommodating articulation between a first bone and a second bone, the joint comprising:
    a first element for attachment to a first bone, the first element having a first surface facing substantially away from the first bone;
    a second element for attachment to a second bone generally along a first axis, the second element having a second surface facing substantially away from the second bone;
    a bearing between and in articulating contact with the first and second surfaces for transferring substantially all of the load from the first element to the second element; and
    a hinge including a member for attachment to the second element and hinged to the first element, the member being secured to the second element such that the hinge transfers relatively negligible load from the first element to the second element in a direction along the first axis and for supporting the first and second elements in a direction transverse the first axis, wherein the prosthesis is for a knee, the articulating contact of the bearing with the first and second surfaces defining articulation between extension and flexion positions of the knee, the bearing and first element being arranged to accommodate articulation of the bearing in congruent contact with the first element during the extension and in incongruent contact during the flexion.

9. A prosthetic joint for accommodating articulation between a first bone and a second bone, the joint comprising:
    a first element for attachment to a first bone, the first element having a first surface facing substantially away from the first bone;
    a second element for attachment to a second bone generally along a first axis, the second element having a second surface lying in a plane transverse the first axis and facing substantially away from the second bone;
    a bearing between and in articulating contact with the first and second surfaces for displacement in a direction transverse to the first axis in response to articulation of the first element relative to the second element; and
    a hinge including an integrally formed member hinged to the first element and movably attached to the second element, said member being arranged to provide negligible load support along said first axis and providing relative stabilizing support for preventing translation of said bones in directions transverse to said first axis.

10. The joint of claim 9 wherein the member is rotationally and axially movably attached to the second element for rotation about and displacement along the first axis.

11. The joint of claim 9 wherein the bearing is in congruent contact with the first element in a first angular extent of displacement of the first element with respect to the bearing and in incongruent contact in a second angular extent of displacement of the first element with respect to the bearing.

12. The joint of claim 9 wherein the bearing comprises a thermoplastic bearing and the first and second elements are metallic, the member passing through the bearing.

13. The joint of claim 12 wherein the bearing comprises a bearing having an opening therethrough, the member passing through the opening, the member and bearing including a mating stop in the opening for stopping the displacement of the bearing at first and second opposing displacement positions of the bearing in a given direction transverse the first axis.

14. The joint of claim 13 wherein the opening has a first dimension in a given direction, the member including a portion in the opening having a second dimension smaller than the first dimension in the given direction.

15. A prosthetic joint for accommodating articulation between a first bone and a second bone, the joint comprising:
- a first element for attachment to a first bone, the first element having a first surface facing substantially away from the first bone;
- a second element for attachment to a second bone generally along a first axis, the second element having a second surface lying in and defining a plane transverse the first axis and facing substantially away from the second bone;
- bearing means between and in articulating contact with the first and second surfaces, the bearing means having a third surface in contact with the first surface and a fourth surface in contact with the second surface, the bearing means and surfaces being constructed for displacement in a direction transverse to the first axis in response to articulation of the first element relative to the second element; and
- an integrally formed hinge hingedly attached to the first element for rotation about a second axis transverse to the first axis, the hinge being attached to the second element for rotation about the first axis and preventing relative translation between the first and second elements in directions transverse to the first axis.

16. The joint of claim 15 wherein the first element has a plurality of contiguous arcuate surfaces for engaging the bearing means-third surface, the arcuate surfaces defining a continuous curvature of a plurality of different radii lying in three contiguous curved segments.

17. A prosthetic joint for accommodating articulation between a first bone and a second bone, the joint comprising:
- a first element for attachment to a first bone, the first element having a first surface facing substantially away from the first bone;
- a second element for attachment to a second bone generally along a first axis, the second element having a second surface lying in and defining a plane transverse the first axis and facing substantially away from the second bone;
- a bearing between and in articulating contact with the first and second surfaces, the bearing having a third surface in contact with the first surface and a fourth surface in contact with the second surface, the bearing and surfaces being constructed for displacement in a direction transverse to the first axis in response to articulation of the first element relative to the second element, the first element having a Plurality of contiguous arcuate surfaces for engaging the bearing third surface, the arcuate surfaces defining a continuous curvature of a plurality of different radii lying in three contiguous curved segments, the first element being rotatable relative to the bearing means between a first rotational alignment and a second rotational alignment, the bearing being constructed with a bearing surface in articulating contact with the first surface such that the first element is in congruent contact with the bearing only for a first selected range of rotation extending from the first rotational alignment of the first element relative to the bearing to an intermediate rotational alignment thereof; and
- a hinge for hinged attachment to the first element for rotation about a second axis transverse the first axis, the hinge further being for attachment to the second element for rotation about the first axis.

18. The joint of claim 17 wherein the first element is in line contact with the bearing in a second selected range of rotation extending from the intermediate rotational alignment toward the second rotational alignment.

19. A prosthetic joint for accommodating articulation between a first bone and a second bone, the joint comprising:
- a first element for attachment to a first bone, the first element having a first surface facing substantially away from the first bone;
- a second element for attachment to a second bone generally along a first axis, the second element having a second surface lying in and defining a plane transverse the first axis and facing substantially away from the second bone;
- bearing means between and in articulating contact with the first and second surfaces, the bearing means having a third surface in contact with the first surface and a fourth surface in contact with the second surface, the bearing means and surfaces being constructed for displacement in a direction transverse to the first axis in response to articulation of the first element relative to the second element; and
- a hinge for hinged attachment to the first element for rotation about a second axis transverse to the first axis, the hinge being for attachment to the second element for rotation about the first axis, and the hinge being coupled to the second element for axial displacement along the first axis in non-load bearing relation to the second element in a direction along said first axis, said coupling between the hinge and the second element preventing relative movement between said first and second elements in directions transverse to the first axis, wherein the bearing means provides sole load transfer between the first and second elements in a direction along the first axis.

20. A prosthetic joint for accommodating articulation between a first bone and a second bone, the joint comprising:
- a first element for attachment to a first bone, the first element having a first surface facing substantially away from the first bone;
- a second element for attachment to a second bone generally along a first axis, the second element having a second surface lying in and defining a plane transverse the first axis and facing substantially away from the second bone, the second element has a frustoconical first cavity centered on the first axis;
- bearing means between and in articulating contact with the first and second surfaces, the bearing means having a third surface in contact with the first surface and a fourth surface in contact with the second surface, the bearing means and surfaces being constructed for displacement in a direction transverse to the first axis in response to articulation of the first element relative to the second element;

a thermoplastic insert having a frustoconical outer surface and being disposed in the first cavity and having a second cavity extending therein and centered on the first axis; and an integrally formed hinge member hingedly attached to the first element for rotation about a second axis transverse to the first axis, the hinge member including a shaft secured to the insert in the second cavity such that the insert prevents movement of the hinge and the first element relative to the second element in directions transverse to the first axis, said insert and said shaft of said hinge member being rotatable relative to the second element about said first axis and being axially displaceable along the first axis, said insert and said hinge member being dimensioned to be in negligible load bearing relation to the second element along said first axis.

21. The joint of claim 20 wherein the member includes a hinge portion and a stop portion intermediate the hinge portion and the shaft, the stop portion for engaging the bearing for stopping the translation of the bearing in two opposing directions transverse the first axis during articulation of the joint.

22. A prosthetic joint for accommodating articulation between a first bone and a second bone, the joint comprising:

a first element for attachment to a first bone, the first element having a first surface facing substantially away from the first bone, the second element having a generally frustoconical recess extending into the second surface;

a second element for attachment to a second bone generally along a first axis, the second element having a second surface facing substantially away from the second bone;

a bearing between and in articulating contact with the first and second surfaces for transferring substantially most of the load from the first bone to the second bone; and a hinge having an integral member for hinged attachment to the first element and a bushing member for fixed attachment to the integral member, the bushing having a frustoconical outer surface generally conforming to the frustoconical recess in the second element, the bushing member being for rotation about a second axis and relative to the second element, the bearing and the bushing member being coupled to the first and second elements such that the bearing transfers the load from the first element to the second element independently of the hinge, the hinge providing stabilizing support for the first and second elements in all directions transverse to the first axis and the bushing member of the hinge being disposed and dimensioned to be in spaced relationship to the second element in at least one range of articulation of the first element relative to the hinge.

23. The joint of claim 22 wherein the second axis is transverse the first axis.

24. The joint of claim 22 wherein the bearing has a planar surface in contact with the second surface and the second surface is planar, the first axis is normal to the plane of the of the second surface.

25. The joint of claim 24 wherein the bearing and the hinge are movably secured to the second element for rotation about the first axis.

26. A prosthetic joint for accommodating articulation between a first bone and a second bone including a first element for attachment to the first bone and having a first surface facing substantially away from the first bone; a second element for attachment to the second bone generally along a first axis and having a second surface facing substantially away from the second bone, a bearing between the first and second elements, the bearing having a third surface in articulating contact with the first surface, a fourth surface in articulating contact with said second surface and a side wall defining a periphery of said bearing and extending continuously between said third and fourth surfaces; said bones exhibiting flexion and extension; and means coupled to the first and second elements for permitting the second element to rotate relative to the first element about the first axis;

rotation limiting means for substantially preventing relative rotation between the first element and the second element about the first axis when said first and second bones are exhibiting said extension, and for permitting gradually greater relative rotation between the first element and the second element about the first axis as the first and second bones undergo flexion, a limiting means consisting of a recess formed in said side wall of said bearing and a projection projecting from said second surface of said second element, the projection abutting the recess in the side wall in said extension so as to preclude relative rotation about said first axis and being spaced from the recess a magnitude that is dependent on the amount of said flexion so as to permit relative rotation therebetween about the first axis; and a hinge means for hinged attachment to the first element and including a bushing member for attachment to the second element, the bushing member permitting rotation relative to the first element about a second axis transverse to the first axis, the bushing member of the hinge means preventing relative movement between the first and second elements in directions transverse to the second axis.

27. The joint of claim 26 wherein the recess and projection are both V-shaped, the recess having a given depth and maximum transverse width, the projection having a thickness in the direction of the recess depth smaller than the depth and a transverse width smaller than the recess maximum transverse width.

28. The joint of claim 26 wherein the first element includes means for attachment to a femur and the second element includes means for attachment to a tibia, said elements for forming a knee joint.

29. The joint of claim 26 wherein the recess is of the same general shape as the projection wherein the projection nests in the recess in a first abutting position in said extension and displaced from the first abutting relation in said flexion.

30. The joint of claim 1 wherein said hinge is configured such that no portion of said hinge is in articulating contact with the second surface of the second element.

31. The joint of claim 9 wherein said hinge is configured such that no portion of said hinge is in articulating contact with the second surface of the second element.

32. The joint of claim 26 further comprising a hinge engaged with said second element for rotation about said first axis and being hingedly connected to said second element for permitting hinged articulation of said first and second elements relative to one another.

* * * * *